United States Patent [19]

Boyle et al.

[11] Patent Number: 4,808,715

[45] Date of Patent: Feb. 28, 1989

[54] 4-QUINAZOLINYLAMINO AND 4-CINNOLINYLAMINO BENZENESULPHONIC ACIDS AND AMIDES

[75] Inventors: John T. A. Boyle, Cookham; Richard S. Todd, Near Slough, both of England

[73] Assignee: John Wyeth & Brother Limited, Maidenhead, England

[21] Appl. No.: 141,178

[22] Filed: Jan. 6, 1988

Related U.S. Application Data

[62] Division of Ser. No. 916,984, Oct. 9, 1986, Pat. No. 4,734,510, which is a division of Ser. No. 744,364, Jun. 13, 1985, Pat. No. 4,640,920.

[30] Foreign Application Priority Data

Jun. 14, 1984 [GB] United Kingdom .................. 8415174
Dec. 19, 1984 [GB] United Kingdom .................. 8432091

[51] Int. Cl.$^4$ .................. C07D 237/28; C07D 239/94
[52] U.S. Cl. ...................................... 544/235; 544/293
[58] Field of Search .................... 544/235, 293

[56] References Cited

U.S. PATENT DOCUMENTS 3,933,829  1/1976  Archibald et al. ................ 546/160
4,684,657  8/1987  Boyle ................................ 544/235

FOREIGN PATENT DOCUMENTS 13765  1/1984  Japan ................................ 544/293

Primary Examiner—Donald G. Daus
Assistant Examiner—E. Bernhardt
Attorney, Agent, or Firm—George Tarnowski

[57] ABSTRACT

Novel quinazoline and cinnoline derivatives having the formula

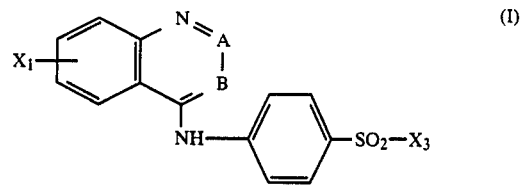

(wherein one of A and B is CH and the other one of A and B is N; $X_1$ is halogen or $CF_3$ and $X_3$ is one of the groups II, III, IV or V

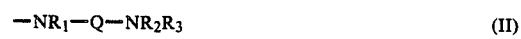

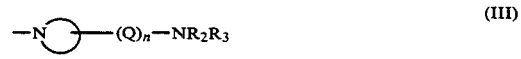

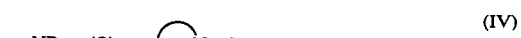

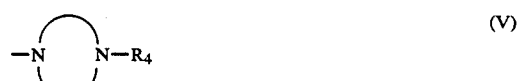

where Q is lower alkylene; $R_1$ is hydrogen or lower alkyl; $R_2$ and $R_3$ are independently lower alkyl or $R_2$ and $R_3$ are a divalent radical such that $HNR_2R_3$ is a secondary cyclic amine with 5 to 7 ring atoms; $R_4$ is lower alkyl; n is 0 or 1; the rings shown in formulae III and IV are piperidine or pyrrolidine optionally substituted by lower alkyl; and the ring shown in formula V is piperazine optionally substituted by lower alkyl) and their pharmaceutically acceptable salts are useful as pharmaceuticals particularly as anti-hypertensives. Novel intermediates are also described including the corresponding sulphonic acids of formula I ((where A, B and $X_1$ are defined above and $X_3$ is OH).

1 Claim, No Drawings

4-QUINAZOLINYLAMINO AND 4-CINNOLINYLAMINO BENZENESULPHONIC ACIDS AND AMIDES

This is a division of application Ser. No. 916,984 filed Oct. 9, 1986 now U.S. Pat. No. 4,734,510, issued Mar. 29, 1988, which is a division of U.S. Ser. No. 744,364, filed June 13, 1985 and now U.S. Pat. No. 4,640,920 issued Feb. 3, 1987.

4-(AZAQUINOLIN-4-YLAMINO)BENZENESULPHONIC ACIDS AND 4-(AZAQUINOLIN-4-YLAMINO)BENZENESULPHONAMIDES

The invention relates to novel quinazoline and cinnoline derivatives that are useful as pharmaceuticals, particularly as anti-hypertensive agents. The invention also provides processes for their preparation, pharmaceutical compositions containing them, novel compounds useful as intermediates for the preparation of the said derivatives and a process for the preparation of the intermediate compounds.

The invention provides, as novel quinazoline and cinnoline derivatives, compounds having the general formula I

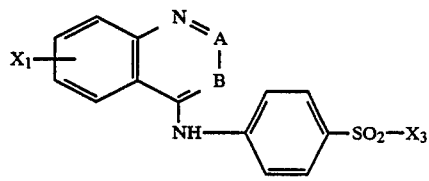

wherein one of A and B is CH whilst the other one of A and B is N; $X_1$ is halogen or trifluoromethyl and $X_3$ represents a group having one of formulae II, III, IV and V

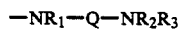  (II)

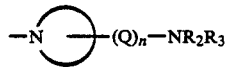  (III)

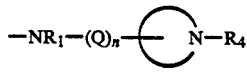  (IV)

  (V)

wherein Q is lower alkylene; $R_1$ is hydrogen or lower alkyl; $R_2$ and $R_3$ are, independently, lower alkyl or $R_2$ and $R_3$ together form a divalent radical such that $R_2R_3NH$ is a secondary cyclic amine with 5 to 7 ring atoms; $R_4$ is lower alkyl; n is 0 or 1; the ring illustrated in formulae III and IV is a piperidine or pyrrolidine ring that may be substituted on one or more carbon ring members by lower alkyl and the ring illustrated in formula V is a piperazine ring that may be substituted on one or more carbon ring members by lower alkyl; and the pharmaceutically acceptable salts thereof. These compounds are indicated for pharmaceutical use, particularly as anti-hypertensive agents.

It will be apparent to those skilled in the art that the above definition of $X_3$ includes moieties possessing an asymmetric carbon atom especially for instance in the cases where Q is present and is a chain of 1 to 4 methylene groups, the chain being monosubstituted by methyl or ethyl or where $X_3$ is of formula IVa or IIIa

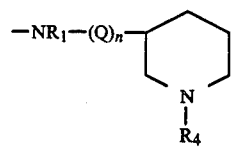  (IVa)

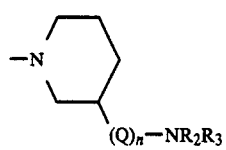  (IIIa)

It is to be understood that formula I is intended to encompass each enantiomer where the compound contains as asymmetric carbon atom and mixtures of enantiomers, for instance, a racemic mixture of enantiomers. Separation of enantiomers can be carried out using general methods known in the literature.

When A is CH whilst B is N the compounds of the invention are quinazoline derivatives. Where A is N whilst B is CH the compounds of the invention are cinnoline derivatives.

$X_1$ may substitute any of the 5, 6, 7 and 8 positions of the quinazoline or cinnoline ring system, but is preferably at the 7- or 8-position, advantageously the 7-position. Where $X_1$ is at the 7-position, formula I may be represented as Ia

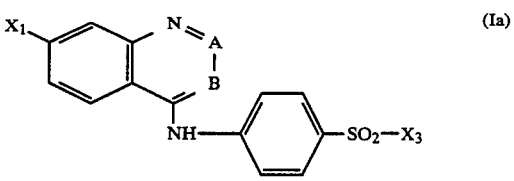

$X_1$ represents halogen, for instance chlorine or bromine, or trifluoromethyl. $X_1$ is preferably chlorine.

In formulae II and IV, $R_1$ represents hydrogen or lower alkyl (for instance methyl, ethyl, propyl, butyl). $R_1$ is preferably hydrogen. In formulae II, III and IV Q is lower alkylene which may be a straight chain i.e. a chain of 1 to 6, preferably 1 to 4, methylene groups. Alternatively Q may be a branched lower alkylene group, for instance, a chain of 1 to 4 methylene groups, the chain being mono- or di-substituted by methyl or monosubstituted by ethyl. $R_2$ and $R_3$ in formulae II and III, when separated, are each lower alkyl (for instance, methyl, ethyl, propyl, butyl). Alternatively $R_2$ and $R_3$ may be joined together to form a divalent radical such that $R_1R_2NH$ is a secondary cyclic amine with 5 to 7 ring atoms, e.g. pyrrolidine, piperidine, morpholine or thiomorpholine. In this case $R_1$ and $R_2$ may together have the formula $-(CH_2)_2-X_2-(CH_2)_2-$ where $X_2$ is $-(CH_2)_n-$, O or S where n is 0, 1 or 2. $R_2$ and $R_3$ are preferably lower alkyl. n in formula III and IV is 0 or 1. $R_4$ in formulae IV and V is lower alkyl (for instance, methyl, ethyl, propyl, butyl). The ring attached to $-(Q)_n-$ in formulae III and IV is a piperidine or pyrrolidine ring whose nitrogen atom is shown in the formula. The ring may be substituted on one or two ring carbon atoms by lower alkyl (for instance methyl, ethyl, propyl, butyl). The ring carbon atoms are preferably unsubstituted. The ring attached to $R_4$ in formula V is a piperazine ring (whose nitrogen atoms are shown in the formula). The piperazine ring may be substituted on one or two ring carbon atoms or lower alkyl (for instance methyl, ethyl, propyl, butyl), but is preferably unsubstituted.

Advantageously $X_3$ is a group having the formula IIa or IVa

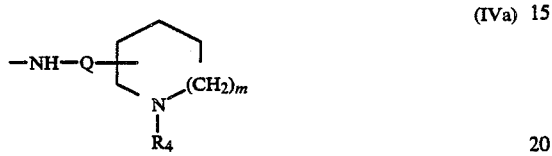

wherein Q is alkylene of 1 to 4 carbon atoms; $R_2$, $R_3$ and $R_4$ are, independently, alkyl of 1 to 4 carbon atoms and m is 0 or 1.

The term "lower" as used herein to refer to such groups as alkyl, alkoxy, alkanoyl and alkylene, indicates that the group contains up to 6, preferably up to 4, carbon atoms. The group may be in the form of a straight chain or may be branched.

The compounds having formula I form acid addition salts with acids. Examples of acid addition salts are those formed from inorganic and organic acids and in particular include the sulphate, hydrochloride, hydrobromide, hydroiodide, nitrate, phosphate, sulphonates (for instance the methanesulphonate or p-toluenesulphonate), acetate, maleate, fumarate, tartrate, malonate, citrate and formate.

The invention also provides, as novel quinazoline and cinnoline derivatives, compounds having the general formula VI

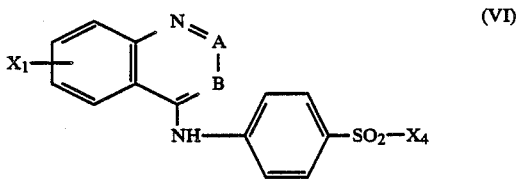

(where $X_1$, A and B are as defined above and $X_4$ is —OH or —$NR_1R_5$ where $R_5$ is hydrogen or a group having the formula —Q—Z where Q is as defined above and Z is a leaving group or atom, preferably a halogen atom or an organosulphonyloxy group, advantageously chlorine, bromine, $C_1$-$C_6$ alkanesulphonyloxy, or substituted or unsubstituted benzenesulphonyloxy, for instance, tosyloxy and $R_1$ is as defined above) and their salts. Such salts include acid addition salts and also sulphonate salts of the sulphonic acid where $X_4$ is —OH. The compounds having formula VI and their salts are useful as intermediates for the preparation of compounds having the formula I and their pharmaceutically acceptable acid addition salts.

A first process according to the invention is for the preparation of compounds having the formula

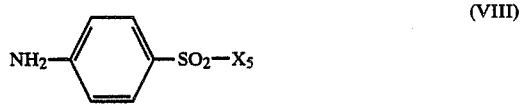

(where A, B and $X_1$ are as defined above and $X_5$ represents $X_3$, —OH or —$NHR_1$ where $X_3$ and $R_1$ are as defined above) or a salt thereof, wherein a compound having the formula VIII

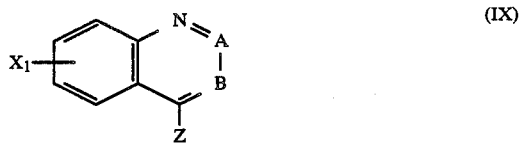

(wherein $X_5$ is as defined above) or a salt thereof is reacted with a compound having the formula IX

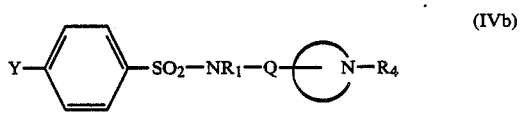

(where $X_1$, A and B are as defined above and Z is a leaving group or atom, preferably a halogen atom such as iodine, bromine or chlorine) and, if desired, a compound having formula VII (where $X_5$ is —OH or —$NHR_1$) is converted into a salt thereof or a compound having formula VII (where $X_5$ is $X_3$) is converted into a pharmaceutically acceptable salt thereof for a salt of a compound having formula VII is converted into the compound having formula VII.

The reaction of the compounds VIII and IX can be carried out in aqueous alcohol with or without acid catalysis. The compounds of formula IX are generally known or, if new, can be prepared in known manner. The sulphonamides (VIII where $X_5$ is —$NHR_1$ or $X_3$) can be prepared by acetylating the sulphanilic acid, converting the N-(acetyl)sulphanilic acid into its sulphonyl chloride derivative, sulphonylating a compound of formula $R_1NH_2$ or $X_3H$ or a salt thereof with the sulphonyl chloride and hydrolysing the sulphonylation product to give the desired aminobenzenesulphonamide. Alternatively, the preparation can be carried out by converting 4-nitrobenzenesulphonic acid into its sulphonyl chloride derivative, sulphonylating a compound of formula $R_1NH_2$ or $X_3H$ or a salt thereof with the sulphonyl chloride and reducing the nitro group to give the desired aminobenzenesulphonamide.

A further class of novel intermediates according to the invention are useful for the preparation of compounds having formula I where $X_3$ has formula IV where n is 1. These novel intermediates have formula IVb

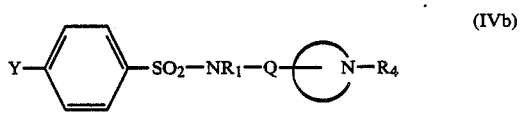

and their acid addition salts where Y is —NH$_2$ (amino), protected amino, for instance lower alkanoylamino, preferably acetamido, or latent amino, preferably nitro and R$_1$, Q, R$_4$ and the ring attached to R$_4$ have the same meanings as in formula IV. The compounds having formula IVb may be prepared by sulphonylating a compound having the formula IVc

  (IVc)

to introduce a sulphonyl group having the formula

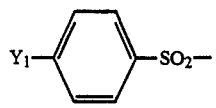

where Y$_1$ is protected amino or latent amino and, where Y is —NH$_2$, converting the protected amino or latent amino group Y$_1$ of the sulphonation product into amino, for instance, by reduction of nitro or hydrolysis of lower alkanoylamino.

The compounds obtained by the aforesaid process where R$_5$ is hydroxy and their salts can be used to prepare the sulphonamide intermediates and end products by forming a sulphonylating agent, preferably the sulphonyl chloride, and sulphonylating ammonia or an appropriate amine or a salt thereof. Accordingly a second process provided by this invention is for the preparation of compounds having the formula X

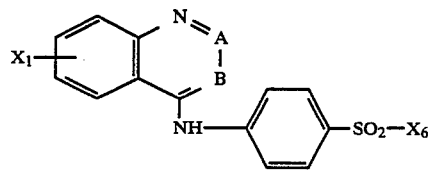 (X)

(where X$_1$, A and B are as defined above and X$_6$ is X$_3$ (as defined above) or —NR$_1$R$_5$ where R$_1$ and R$_5$ are as defined above) and the salts thereof. According to this process a compound of general formula X$_6$H (XI) where X$_6$ is as defined above or a salt thereof is sulphonylated to introduce the sulphonyl group of general formula XII

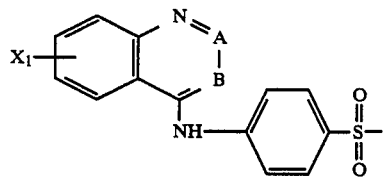 (XII)

(where X$_1$, A and B are as defined above) and, if desired, a compound having formula X is converted into a salt thereof or a salt of a compound having formula X is converted into the compound having formula X.

As sulphonylating agent, the sulphonyl chloride is preferably used. The reaction can be carried out in known manner for sulphonylation of ammonia and amines. The sulphonylation can be carried out in a suitable solvent, for instance, chloroform or methylene chloride, in the presence of a base to neutralise the hydrogen chloride formed. The base may be provided by using, for instance, an alkali metal carbonate or bicarbonate or a tertiary amine, for instance, triethylamine or an excess of the basic compound having formula X$_6$H.

The chemical intermediate sulphonamides of the invention (formula VI where X$_4$ is —NR$_1$R$_5$) may be prepared as described above with reference to formula VII where X$_5$ is —NHR$_1$ of formula X where X$_6$ is —NR$_1$R$_5$. In the case where X$_4$ is —NHR$_1$ the sulphonamide may be converted into some of the end product sulphonamides by alkylation under basic conditions. Accordingly a third process provided by the invention is for the preparation of a compound having the general formula XIII

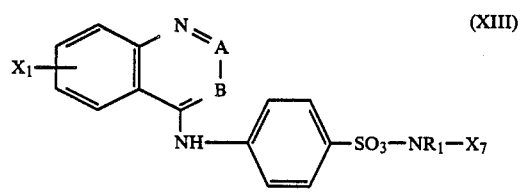 (XIII)

(wherein X$_1$, A, B and R$_1$ are as defined above and X$_7$ represents a group having the formula XIV or XV

 (XIV)

 (XV)

(wherein Q, n, R$_2$, R$_3$, R$_4$ and the ring shown in formula XV have the same meanings as defined under formulae II and IV) or a pharmaceutically acceptable salt thereof, wherein a compound having the formula XVI

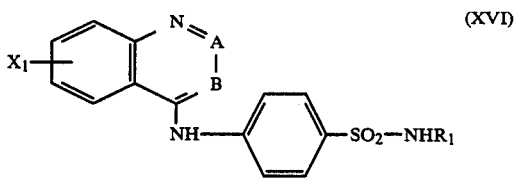 (XVI)

(where X$_1$, X$_2$, A, B and R are as defined above) is reacted with a compound having the formula Z—X$_7$ (XVII) (where Z and X$_7$ are as defined above) under basic conditions and, if desired, the resultant compound of formula XIII is converted into a pharmaceutically acceptable salt thereof.

The above process may be carried out in known manner for the alkylation of sulphonamides. The product XIII may be recovered as such or as an acid addition salt by known isolation procedures.

The intermediate sulphonamides of formula VI where X$_4$ is —NH$_2$ and the sulphonamides of formula XIII (where R$_1$ is hydrogen) may also be alkylated to introduce R$_1$ as lower alkyl. Accordingly the invention also provides a process for the preparation of a compound having the formula XVIII

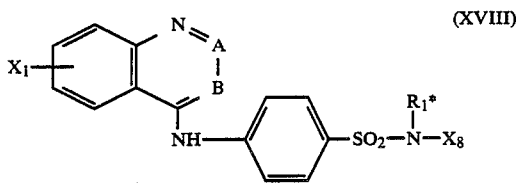

(XVIII)

(where $X_1$, A and B are as defined above; $R_1^*$ is lower alkyl and $X_8$ is $X_7$ or hydrogen) or a salt thereof, wherein a compound having the formula XIX

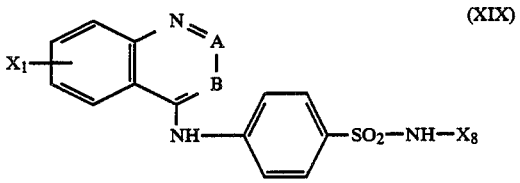

(XIX)

(wherein $X_1$, $X_8$, A and B are as defined above) is reacted with an alkylating agent under basic conditions to introduce the lower alkyl group $R_1^*$ and, if desired, the resultant compound having formula XVIII is converted into a salt thereof. The process may be carried out in accordance with known procedures for alkylation of sulphonamides. The product (XIX) may be recovered as such or as an acid addition salt by known isolation procedures.

It will be apparent that the sulphonamides of formula I where $X_3$ is of formula II or IV in which $R_1$ is lower alkyl and their pharmaceutically acceptable salts can be prepared from corresponding sulphonamides whose sulphonamide nitrogen atom is unsubstituted by applying the third and fourth processes of the invention in either order. Either one of $X_7$ and the lower alkyl group represented by $R_1$ is introduced as a first step and the other one of $X_7$ and the lower alkyl group is introduced as a second step.

The intermediate sulphonamides having formula VI where $X_4$ is $-NR_1-Q-Z$ can also be used to prepare some of the end compounds of the invention. Accordingly the invention also provides a process for the preparation of a compound having the formula

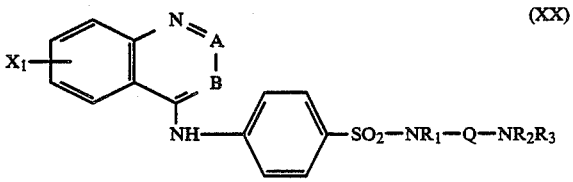

(XX)

(wherein $X_1$, A and B are as defined under formula I and $R_1$, $R_2$, $R_3$ and Q are as defined under formula II) or a pharmaceutically acceptable salt thereof, wherein a compound having the formula

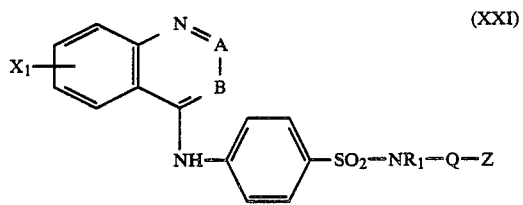

(XXI)

wherein $X_1$, A, B, Q and $R_1$ are as defined above under formula XX, and Z is as explained under formula VI) is reacted with a compound having the formula $HNR_2R_3$ (XXII) in which $R_2$ and $R_3$ are as defined under formula XX or a salt thereof and, if desired, a compound having formula XX is converted into a pharmaceutically acceptable salt thereof or a salt of a compound having formula XX is converted into a compound having formula XX. The reaction of the compound XXI with the amine XXII can be carried out in conventional manner for the conversion of secondary amines into tertiary amines, preferably under pressure.

The novel compounds having general formula I and their pharmaceutically acceptable salts are indicated for use as anti-hyertensive agents. The compounds may be tested for their response on the blood pressure of spontaneously hypertensive rats in the following procedure:

The blood pressure of male or female conscious rats that are spontaneously hypertensive are measured in a 39° C. constant temperature housing by means of a tail cuff. Rats with systolic pressures below 155 mm Hg are not used. Groups of rats (4 per group) are dosed orally with the test substance in a suitable vehicle or with vehicle alone. Systolic pressures are recorded before dosing and at selected time points afterwards (2 hours, 6 hours and 24 hours).

The following table indicates results obtained in the procedure described above:

| Compound (identified by Example No.) | 0.015 Dose (millimoles per Kg) | Blood pressure (as % of blood pressure before dosing) | | |
|---|---|---|---|---|
| | | After 2 hours | After 6 hours | After 24 hours |
| 3 | 0.03 | 80 | 67 | 102 |
|   | 0.03 | 77 | 70 | 85 |
|   | 0.015 | 84 | 75 | 86 |
|   | 0.003 | 92 | 85 | 91 |
| 5 | 0.03 | 83 | 75 | 95 |
| 6 | 0.03 | 77 | 67 | 97 |
| 7 | 0.03 | 71 | 73 | 98 |
| 8 | 0.03 | 98 | 85 | 107 |
| 9 | 0.03 | 71 | 62 | 70 |
| 16b | 0.03 | 74 | 58 | 85 |

The invention also provides a pharmaceutical composition comprising a compound having formula I or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid or a mixture of a solid and a liquid.

Solid form compositions include powders, granules, tablets, capsules (e.g. hard and soft gelatin capsules), suppositories and pessaries. A solid carrier can be, for example, one or more substances which may also act as flavouring agents, lubricants, solubilisers, suspending agents, fillers, glidants, compression aides, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycerol and glycols) and their derivatives and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form. The quantity of the active ingredient in unit dose of composition may be varied or adjusted from 0.5 mg or less to 750 mg or more, according to the particular need and the activity of the active ingredient. The invention also includes the compounds in the absence of the carrier where the compounds are in unit dosage form.

The invention is illustrated by the following examples:

EXAMPLE 1

4-(7-Chloro-4-quinazolinylamino)benzenesulphonic acid

Sulphanilic acid (12.1 g, 0.07 mole) was partly dissolved in 280 milliliters of aqueous ethanol (50% by volume) at reflux and 4,7-dichloroquinazoline (13.9 g, 0.07 mole) was added rapidly in a few portions. The mixture was refluxed for a further 15 minutes, cooled and filtered to give the title compound hemihydrate of melting point greater than 300° C.

Analysis: Calculated for $C_{14}H_{10}ClN_3O_3S.\frac{1}{2}H_2O$: C, 48.8%; H, 3.22%; N, 12.2%. Found: C, 48.7%; H, 3.32%; N, 11.8%.

The sulphonyl chloride hydrochloride derivative of the title compound may be prepared by the following procedure. The title compound (12.6 g, 0.036 mole) was heated to reflux for 4 hours in thionyl chloride (90 ml) containing dimethylformamide (0.75 ml). Excess thionyl chloride was evaporated under reduced pressure and the solid was washed with toluene to give the sulphonyl chloride hydrochloride (13.9 g).

EXAMPLE 2

4-(7-Chloro-4-cinnolinylamino)benzenesulphonic acid

Sulphanilic acid (1.95 g) in water (75 ml) and ethanol (10 ml) at 70° C. was treated with 4,7-dichlorocinnoline (2.2 g) and ethanol (10 ml) was added. The resultant green suspension was stirred vigorously overnight at 70° C. The mixture was cooled, and the solid was filtered, washed with water and dried at room temperature to give 3.45 g of the title compound as the monohydrate, melting point greater than 280° C.

Analysis: Calculated for $C_{14}H_{10}ClN_3O_3S.H_2O$: C, 47.53%; H, 3.42%; N, 11.88%. Found: C, 47.4%; H, 3.36; N, 11.71%.

The sulphonyl chloride hydrochloride derivative of the title compound is prepared from the title compound in a similar manner to that used in Example 1, last paragraph.

EXAMPLE 3

4-(7-Chloro-4-quinazolinylamino)-N-(2-diethylaminoethyl)benzenesulphonamide 4-(7-Chloro-4-quinazolinylamino)benzenesulphonyl chloride hydrochloride (36.0 g obtainable from the title compound of Example 1) and methylene chloride (180 ml) were cooled under nitrogen to 5° C. N,N-Diethylethylenediamine (35.4 g) was then added at 5°–10° C. over 20 minutes to give a light yellow solution. The solution was stirred for 2 hours under nitrogen at 5° to 15° C. and then water (200 ml) was added. A white solid precipitated. The mixture was cooled to 10° C. and the solid was filtered off, washed with water (2×40 ml) and with chloroform (2×40 ml) and dried in an oven to give 279 g of title compound.

A 27 g sample of the title compound was recrystallised and converted into the hydrochloride by the following procedure. The sample was dissolved in refluxing acetone (350 ml). The mixture was filtered hot and solvent was distilled off to give a volume of 100 ml of mixture. The mixture was cooled to about 10° C. and then filtered. The white solid was collected, washed with acetone (2×50 ml) and dried in an oven to give 23.5 g of title compound.

The recrystallised title compound was suspended in isopropyl alcohol (100 ml) and water (50 ml). Concentrated hydrochloric acid was added until the pH of the mixture was 1. The mixture was stirred for 20 minutes and filtered and the collected solid was washed with water (2×15 ml), isopropyl alcohol (2×30 ml) and dried in an oven overnight to yield 18.5 g of the title compound hydrochloride.

A sample of the title compound was converted into its hydrochloride by dissolving in warm ethanol and adding ethereal hydrogen chloride to give the title compound as its hydrochloride, three quarters ethanolate, m.p. 203° C.

Analysis: Found: C, 51.5%; H, 5.86%, N, 13.5% $C_{20}H_{24}ClN_5O_2S \cdot HCl \cdot \frac{3}{4}C_2H_6O$ requires C, 51.1%; H, 5.88%; N, 13.9%.

EXAMPLE 4

1-[4-(7-Chloro-4-quinazolinylamino)benzenesulphonyl]-4-methylpiperazine

N-Methylpiperazine (1.0 g, 0.01 mole) was dissolved in chloroform (50 ml). Sodium carbonte (10 g) was dissolved in water (50 ml). The solutions were combined and cooled to 10° C. 4-(7-Chloro-4-quinazolinylamino)benzenesulphonyl chloride hydrochloride (3.85 g, 0.01 mole) was added in portions to the vigorously stirred solution. Stirring was continued for one hour. The chloroform layer was separated, dried and evaporated. The resulting gummy solid was redissolved in chloroform and chromatographed on an alumina column. Elution with chloroform gave a first band which was discarded. The second band was obtained as a low melting solid, which was converted to the hydrochloride by dissolving in ethanol and adding ethereal hydrogen chloride to give the title compound as the sesquihydrochloride (650 mg) m.p. 237°-239° C.

Analysis: Found: C, 48.3%; H, 4.58%; N, 14.8% $C_{19}H_{20}ClN_4O_2S \cdot 3/2HCl$ requires C, 48.7%; H, 4.80%; N, 14.7%.

EXAMPLE 5

4-(7-Chloro-4-quinazolinylamino)-N-(1-ethyl-3-piperidyl)benzenesulphonamide

3-Amino-1-ethylpiperidine (1.1 g, 0.0087 mole) was dissolved in chloroform (50 ml), sodium carbonate (10 g) was dissolved in water (50 ml) and the combined solutions were cooled to 10° C. 4-(7-Chloro-4-quinazolinylamino)benzenesulphonyl chloride hydrochloride (3.4 g, 0.0087 mole) was added in portions to the vigorously stirred solutions. Stirring was continued for one hour. The chloroform layer was separated, dried and evaporated to give a gummy solid which was triturated twice with benzene to give a colourless solid (1.1 g). This was found to contain benzene. The solid was therefore chromatographed through an alumina column and eluted with chloroform to give a solid which was converted to the hydrochloride by dissolving in ethyl acetate and adding ethereal hydrogen chloride to give the title compound as its dihydrochloride (700 mg). No definite m.p. was exhibited but the compound softens above 175° C.

The infra-red spectrum of the title compound exhibits prominent peaks at 2672, 1614, 1561, 1439, 1376, 1156, 1096, 880, 702 and 600 cm$^{-1}$.

Analysis: Found: C, 48.2% H, 5.04%; N, 13.1% $C_{21}H_{24}ClN_5O_2S \cdot 2HCl \cdot \frac{1}{4}H_2O$ requires C, 48.2%; H, 5.10%; N, 13.4%.

EXAMPLE 6

4-[7-Chloro-4-cinnolinylamino]-N-(2-diethylaminoethyl)benzenesulphonamide

A mixture of anhydrous sodium carbonte (3.08 g) and N,N-diethylethylenediamine (0.43 ml) in chloroform (30 ml) was vigorously stirred at 5° C. and treated with 4-(7-Chloro-4-cinnolinylamino)benzenesulphonyl chloride hydrochloride (1.0 g). The mixture was stirred at room temperature for 1½ hours and then filtered. The filtrate was evaporated to give a residue that crystallised from ethanol to give the title compound (0.456 g), m.p. 175°–76° C.

Analysis: Found: C, 55.3%; H, 5.6%; N, 16.0% $C_{20}H_{24}ClN_5O_2S$ requires C, 55.36%; H, 5.57%; N, 16.14%.

EXAMPLE 7

4-[7-Chloro-4-cinnolinylamino]-N-(1-ethyl-3-piperidyl)benzenesulphonamide

3-Amino-1-ethylpiperidine (0.4 ml) in chloroform (15 ml) was treated with anhydrous sodium carbonate (2.94 g) in water (15 ml) and cooled to 3° C. The mixture was vigorously stirred and treated with 4-(7-chloro-4-cinnolinylamino)benzenesulphonylchloride hydrochloride (1.0 g). The dark orange mixture was stirred at 3° C. for 15 minutes, then at room temperature for 45 minutes. During this period the colour lightened considerably. The chloroform layer was separated and dried over magnesium sulphate. The residue on evaporation solidified when triturated with methanol, to give the title compound (0.5 g), m.p. 213°–15° C. (with decomposition).

Analysis: Found: C, 56.4; H, 5.6; N, 15.65% $C_{21}H_{24}ClN_5O_2S$ requires C, 56.56; H, 5.42; N, 15.7%.

EXAMPLE 8

4-(7-Chloro-4-quinazolinylamino)-N-[2-(1-pyrrolidinyl)ethyl]benzenesulphonamide 4-(7-Chloro-4-quinazolinylamino)benzene sulphonyl chloride, hydrochloride (3.5 g, 0.011 mole) was added portionwise to a well-stirred mixture of sodium carbonate (11.5 g) in water (120 ml) and N-(2-aminoethyl)-pyrrolidine (1.26 g, 0.01 mole) in chloroform (120 ml) at about 10° C. After 1 hour at room temperature, the mixture was filtered. The chloroform layer was separated, dried (MgSO$_4$) and evaporated under reduced pressure to give a gum. Trituration from ethyl acetate gave a white solid (1.14 g) which could be crystallised from ethanol-water, m.p. 203°–204.5° C.

Analysis: Found: C, 56.0%; H, 5.40%; N, 16.1% $C_{20}H_{22}ClN_5O_2S$ requires: C, 55.6%; H, 5.13%; N, 16.2%.

EXAMPLE 9

4-(7-Chloro-4-quinazolinylamino)-N-[(2-(1-ethyl)pyrrolidinyl)methyl]benzenesulphonamide 4-(7-Chloro-4-quinazolinylamino)benzenesulphonyl chloride hydrochloride (13.0 g, 0.033 mole) was added portionwise to a well stirred mixture of sodium carbonate (33 g) in water (350 ml) and 2-(aminomethyl)-1-ethyl-pyrrolidine (4.3 g, 0.033 mole) in chloroform (350 ml), at 10° C. After 1 hour at room temperature, the mixture was filtered and the solid washed with water, then dried (vacuum oven). Recrystallisation from ethanol gave the title compound (6.74 g), m.p. 199°–201° C.

Analysis: Found: C, 56.3%; H, 5.43%; N, 15.6%
$C_{21}H_{24}ClN_5O_2S$ requires: C, 56.6%; H, 5.42%; N, 15.7%

EXAMPLE 10

N-(3-Chloropropyl)-4-(7-chloro-4-quinazolinylamino)-Benzenesulphonamide 4-(7-Chloro-4-quinazolinylamino)benzenesulphonyl chloride hydrochloride (11.7 g, 0.03 mole) was added portionwise to a well stirred mixture of sodium carbonate (45 g) in water (350 ml) and 3-chloropropylamine hydrochloride (3.9 g, 0.03 mole) in chloroform (350 ml) was added at 10° C. After about 1 hour at room temperature, the mixture was filtered and the solid was washed with water and then dried to give 7.4 g of the title compound. A sample was recrystallised from a mixture of ethanol and water to give the title compound, m.p. 168°–171° C.

Analysis: Found: C, 50.0%; H, 4.07%; N, 13.5% $C_{17}H_{16}Cl_2N_4O_2S$ requires C, 49.6%; H, 3.92%; N, 13.6%.

EXAMPLE 11

4-(7-Chloro-4-quinazolinylamino)-N-(3-diethylaminopropyl)benzenesulphonamide

A solution of the title compound of Example 10 (4.1 g, 0.01 mole) in ethanol (120 ml) containing diethylamine (20 ml, 0.2 mole) was heated to 120° in a bomb for 5 hours and then left at room temperature overnight. Evaporation of the solvent under reduced pressure gave a crude red solid, which was chromatographed with alumina (basic) and 1% ethanol/chloroform. Recrystallisation from ethanol-water gave a white solid (1.43 g). A second recrystallisation of a 1.0 g sample from ethanol/water gave the title compound as the hemihydrate (0.84 g), melting point 163°–165° C.

Analysis: Found: C, 54.9%, H, 5.61%; N, 15.3% $C_{21}H_{26}ClN_5O_2S.\frac{1}{2}H_2O$ requires C, 55.2%; H, 5.96%; N, 15.3%.

EXAMPLE 12

4-(7-Chloro-4-quinazolinylamino)-N-(2-diethylaminoethyl)benzenesulphonamide (a)
N-(2-Chloroethyl)-4-(7-Chloro-4-quinazolinylamino)-benzenesulphonamide This compound is prepared in a similar manner to Example 10 using 2-chloroethylamine hydrochloride (0.03 moles) instead of 3-chloropropylamine hydrochloride.

(b)
4-(7-Chloro-4-quinazolinylamino)-N-(2-diethylaminoethyl)benzenesulphonamide

This compound can be prepared in a similar manner to Example 11 using the title compound of part (a) [0.01 mole] instead of the title compound of Example 10 and a bomb temperature of 100° C. instead of 120° C.

EXAMPLE 13

4-(7-Chloro-4-cinnolinylamino)-N-(2-diethylaminoethyl)benzenesulphonamide (a)
4-(7-Chloro-4-cinnolinylamino)-N-(2-chloroethyl)benzenesulphonamide This compound is prepared in a similar manner to the procedure of Example 10 using equimolar quantities of 2-chloroethylamine hydrochloride instead of 3-chloropropylamine hydrochloride and 4-(7-chloro-4-cinnolinylamino)benzenesulphonyl chloride hydrochloride instead of 4-(7-chloro-4-quinolinylamino)benzenesulphonyl chloride.

(b)
4-(7-Chloro-4-cinnolinylamino)-N-(2-diethylaminoethyl)benzenesulphonamide

This compound is prepared in a similar manner to Example 11 using the title compound of part (a) [0.01 mole] instead of the title compound of Example 10 and a bomb temperature of 100° C. instead of 120° C.

EXAMPLE 14

(a) 4-(6-Chloro-4-quinazolinylamino)benzenesulphonic acid 4,6-Dichloroquinazoline (5.9 g, 0.03 mole) was added portionwise to sulphanilic acid (5.2 g, 0.03 mole) in 50% aqueous ethanol (200 ml) at 90° C. with stirring. The mixture was refluxed for 2 hours, cooled and filtered. The solid was washed with 50% aqueous ethanol and dried in an oven to give the title compound (9.2 g) as the hemihydrate m.p. greater than 300° C.

Analysis: Found: C, 48.6%; H, 3.28%; N, 11.9% $C_{14}H_{10}ClN_3O_3S$ requires C, 48.8%; H, 3.22%; N, 12.2%.

(b)
4-(6-Chloro-4-quinazolinylamino)-N-(2-diethylaminoethyl)benzenesulphonamide

The sulphonyl chloride hydrochloride derivative of the sulphonic acid or part (a) was used to sulphonylate N,N-diethylethylenediamine using a similar procedure to Example 8. The crude product obtained after evaporation of solvent from the chloroform layer was a brown solid which was purified by column chromatography (basic alumina: 1% ethanol/chloroform) to give a creamy white solid. Recrystallisation from ethanol/water gave the title compound hemihydrate, m.p. 110°–113° C. Analysis: Calculated for $C_{20}H_{24}ClN_5O_2S.\frac{1}{2}H_2O$ C, 54.2%; H, 5.69%; N, 15.8%. Found C, 54.3%; H, 5.64%; N, 16.1%.

EXAMPLE 15

(a)
4-Acetylamino-N-[(1-ethyl-2-pyrrolidinyl)methyl]benzenesulphonamide

4-Acetylaminobenzenesulphonyl chloride (7.3g, 0.03 mole) was added portionwise to a well stirred mixture of aqueous sodium carbonate (21.2 g. in 250 ml of water) and 2-aminomethyl-1-ethylpyrrolidine (4.0 g. 0.03 mole) in chloroform (250 ml) at about 10°. The ice bath used for cooling was removed. After 2 hours the chloroform layer was separated, dried (MgSO₄) and then evaporated under reduced pressure to give a gum, which slowly crystallised (11.6 g). Recrystallisation from cold ethanol, followed by recrystallisation from water gave the pure title compound m.p. 94°–96° C.

Analysis Found: C, 52.5%; H, 7.39%; N, 12.0% $C_{15}H_{23}N_3O_3S.H_2O$ requires C, 52.5%; H, 7.34%; N, 12.2%.

(b)

4-Amino-N-[(1-ethyl-2-pyrrolidinyl)methyl[benzenesulphonamide

4-Acetylamino-N-[(1-ethyl-2-pyrrolidinyl)methyl]-benzenesulphonamide (6.5 g, 0.02 mole) was dissolved in 50 ml of 2N aqueous sodium hydroxide. The solution was heated to reflux, with stirring, for 1½ hours. The solution was cooled and the pH was adjusted to about 8 with hydrochloric acid (2N). The mixture was extracted with chloroform (3×50 ml) and the combined extracts were dried (MgSO$_4$) and evaporated under reduced pressure to give a solid (4.9 g). The solid was purified by column chromatography (basic Al$_2$O$_3$: 1% ethanol/chloroform), followed by recrystallisation from water, to give the pure title compound m.p. 109°–110° C.

Analysis Found: C, 55.2%; H, 7.59%; N, 15.1% $C_{13}H_{21}N_3O_2S$ requires C, 55.1%; H, 7.47%; N, 14.8%.

EXAMPLE 16

(a)

4-(7-Trifluoromethyl-4-quinazolinylamino)benzenesulphonic acid 0.8 grams of sulphanilic acid and an equimolar quantity of 4-chloro-7-trifluoromethylquinazoline were heated in 20 ml of 50% aqueous ethanol at 100° C. for 2 hours. The suspension was cooled and the solid was filtered off, washed with water and dried to give 1.03 g of the title compound. The sulphonyl chloride hydrochloride derivative for use in part (b) below was prepared in similar manner to Examples 1 and 2.

(b)

N-[(1-ethyl-2-pyrrolidinyl)methyl]-4-(7-trifluoromethyl-4-quinazolinylamino)benzamide A mixture of 2-aminomethyl-1-ethylpyrrolidine (0.34 ml; 0.00235 mole), anhydrous sodium carbonate (3.5 g) and chloroform (100 ml) was cooled on an ice bath and treated with 4-(7-trifluoromethyl-4-quinazolinylamino)-benzene sulphonylchloride hydrochloride (1.0 g; 0.00235 mole) with vigorous stirring. The mixture was stirred at ambient temperature for 4 hours and then filtered. The residue on evaporation of the solvent was triturated with ether and the resulting solid was filtered off, washed with a little ether and dried to give the quarter hydrate of the title compound (0.28 g), melting point 150°–152° C.

Analysis Found: C, 54.4%; H, 5.0%; N, 14.8%; $C_{22}H_{24}F_3N_5O_2S.\frac{1}{4}H_2O$ requires C, 54.59%; H, 5.1%; N, 14.47%.

We claim:

1. A compound having the formula:

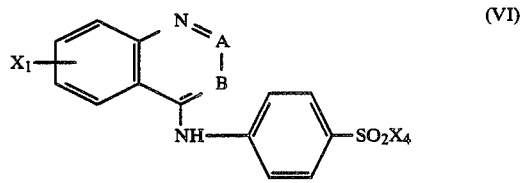

(VI)

and the pharmaceutically acceptable salts thereof, wherein $X_1$ is selected from halogen and trifluoromethyl; $X_4$ is selected from —OH and —NR$_1$R$_5$; R$_1$ is selected from hydrogen and lower alkyl; R$_5$ is selected from hydrogen and a group having the formula —Q—Z; Q represents lower alkylene; one of A and B is CH whilst the other one of A and B is N; and Z is a halogen atom or $C_1$–$C_6$ alkanesulphonyloxy, or substituted or unsubstituted benzenesulphonyloxy.

* * * * *